Jan. 18, 1955 E. S. BOERNER Plant Pat. 1,340
ROSE PLANT
Filed April 19, 1954
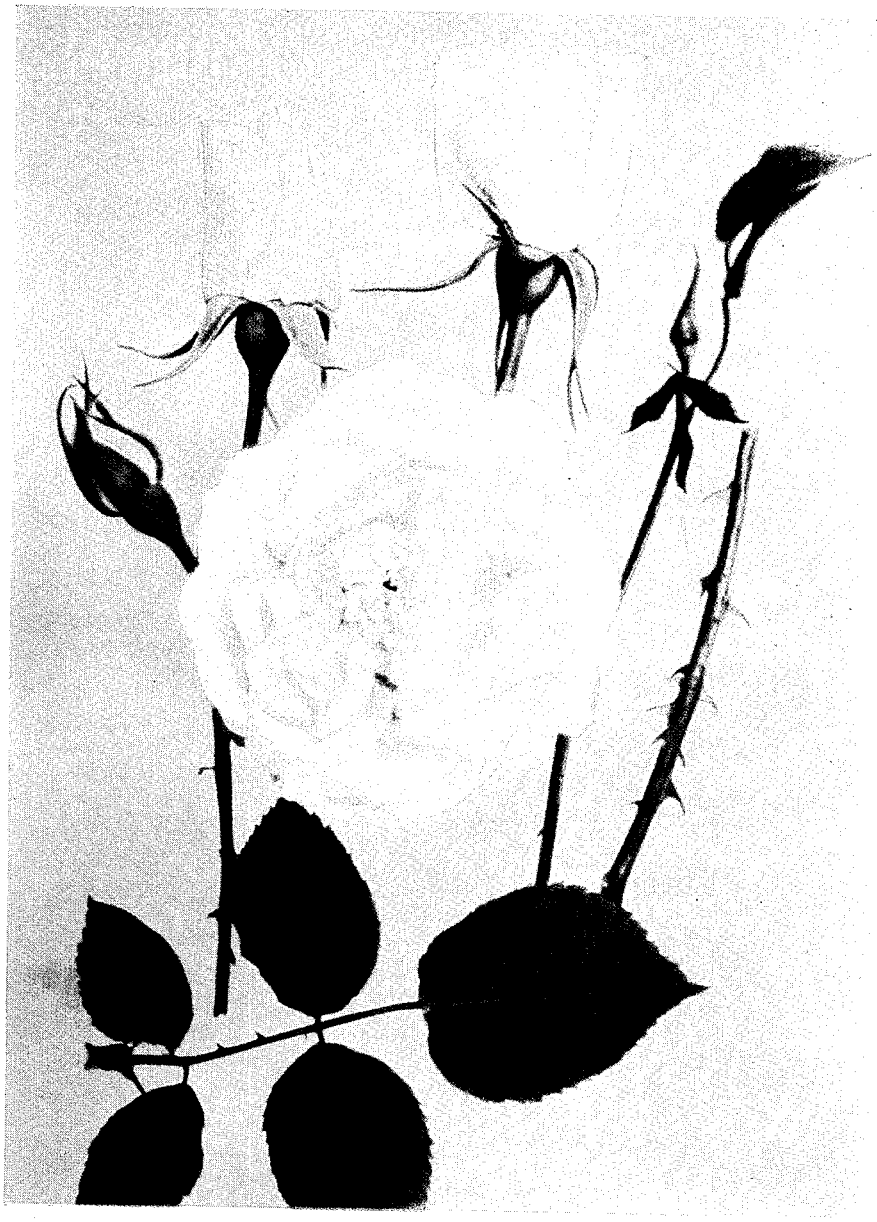
Inventor
E. S. Boerner
By: Robb & Robb
Attorneys.

United States Patent Office

Plant Pat. 1,340

Patented Jan. 18, 1955

1,340

ROSE PLANT

Eugene S. Boerner, Newark, N. Y., assignor to Jackson & Perkins Company, Newark, N. Y., a corporation of New York Application April 19, 1954, Serial No. 424,286

1 Claim. (Cl. 47—61)

The present invention relates to a new and distinct variety of rose plant of the hybrid tea class, which was originated by me by crossing an unnamed and unpatented hybrid tea seedling with the variety "Serenade" (Plant Patent No. 852).

The primary objective of this cross was to produce a new variety of rose plant having vigorous-growing and free-blooming habits, and which bears flowers of a new and distinctive color. The unnamed seedling, above referred to, was selected as one of the parents of my new variety by reason of the fact that it is characterized by its free production of flowers of very fine shape, but the plant of that variety is relatively small and the color of its flowers is not attractive. However, by crossing that variety with the variety "Serenade," my objectives were fully achieved, as evidenced by the vigorous habit of growth of the plants of my new variety, the large size and abundance of its flowers, and the richness, intensity and distinctiveness of the flower color, which, in the case of the buds, is Rose Red, lightly overcast with Jasper Red, while in the case of the fully open blooms, the inside surfaces of the petals are Ochraceous Salmon lightly overcast with Mikado Orange and Eugenia Red, and the outside surfaces of the petals are Eugenia Red lightly overcast with Coral Red. The general color tonality of the flowers of my new variety, as observed from a distance, is Ochraceous Salmon, lightly overcast with Mikado Orange. The vigorous habit of growth of the plants of my new variety is quite unusual and unique in the case of rose plants which bear flowers in this color range.

The foregoing characteristics definitely distinguish my new variety from its parents, as well as from all other varieties of its class.

Asexual reproduction of the new variety, as performed by budding at Newark, New York, and also at Pleasanton, California, shows that the foregoing characteristics and distinctions come true to form and are established and transmitted through succeeding propagations.

The accompanying drawing shows typical specimens of the flowers, stems and foliage of my new variety in different stages of development, and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—An unnamed hybrid tea seedling.
- *Pollen parent.*—"Serenade."

Classification:
- *Botanic.*—Hybrid tea.
- *Commercial.*—Hybrid tea.

FLOWER (Observations made from specimens grown in greenhouses at Newark, New York, in the early part of the month of April, and in the early morning.)

Blooming habit: Recurrent—continuous.

Bud:
- *Size.*—Large.
- *Form.*—Ovoid; is not affected by wet or hot weather.
- *Color.*—When sepals first divide—Scarlet Red, Plate 1. When petals begin to unfurl—Rose Red, Plate 12, lightly overcast with Jasper Red, Plate 13. When half blown: inside of petals—Salmon Orange, Plate 2; reverse of petals—Rose Red, Plate 12, lightly overcast with Scarlet, Plate 1.
- *Sepals.*—Slightly branched; curl back when petals begin to unfurl. Color: inside—Kildare Green, Plate 31; outside—Light Elm Green, Plate 17.
- *Calyx.*—Color—Oil Green, Plate 5. Shape—apple. Size — broad. Aspect — smooth. Odor when rubbed—none.
- *Peduncle.* — Length — medium. Aspect — smooth. Strength—erect; slender. Color—Courge Green, Plate 17.
- *Opening.*—Opens up well; is not affected by adverse weather conditions.

Bloom:
- *Size.*—Large; average size when fully expanded—from 5½ to 6 inches.
- *Borne.*—Sometimes singly and sometimes several together.
- *Stems.*—Medium length; normal strength.
- *Form.*—(*when first open*).—Open. Permanence—retains its form to the end.
- *Petalage.*—Double (full but open center); from 45 to 50 petals under normal conditions.
- *Color.*—Center of flower—Eugenia Red, Plate 13. Outer petals—Pale Orange Yellow, Plate 3, lightly overcast with Light Orange Yellow, Plate 3, and with the outer edges of the petals lightly overcast with Eugenia Red, Plate 13. Base of petals (aiglet)—Lemon Chrome, Plate 4. Inside of petals—Ochraceous Salmon, Plate 15, lightly overcast with Mikado Orange, Plate 3 and Eugenia Red, Plate 13. Reverse of petals—Eugenia Red, Plate 13, lightly overcast with Coral Red, Plate 13. General tonality from a distance—Ochraceous Salmon, Plate 15, lightly overcast with Mikado Orange, Plate 3 and Eugenia Red, Plate 13.
- *Discoloration.*—General tonality at end of first day—Ochraceous Salmon, Plate 15, overcast with Mikado Orange, Plate 3 and Eugenia Red, Plate 13. Second day—Ochraceous Salmon, Plate 15, lightly overcast with Mikado Orange, Plate 3 and Eugenia Red, Plate 13. Third day—Pale Orange Yellow, Plate 3, lightly overcast with Light Orange Yellow, Plate 3.

Petals:
- *Texture.*—Leathery; is not affected by wet or hot weather.
- *Appearance.*—Inside—satiny. Outside—velvety.
- *Form.*—Oval.
- *Arrangement.* — Imbricated (regularly arranged shingle-like). Petaloids in center—none.
- *Persistence.*—Drop off cleanly.
- *Fragrance.*—Moderate. Nature—tea (average hybrid tea scent).
- *Lasting quality.* — On the plant — long. As cut flower—long.

GENITAL ORGANS

Stamens, anthers: Large; few; tucked in calyx. Color—Light Cadmium, Plate 4.

Stamens, filaments (threads). Long. Color—Cadmium Orange, Plate 3.

Pollen: Color—Buff Yellow, Plate 4.

Styles: Columnar; uneven length; medium length; thin.

Stigmas: Color—Baryta Yellow, Plate 4.

Ovaries: All enclosed in calyx.

Hips: None.

Seeds: None.

PLANT

Form: Bush.

Growth: Vigorous; upright.

Foliage: 5–7 leaflets.
- *Size.*—Medium.
- *Quantity.*—Normal.
- *Color.*—New foliage: upper side—Oxblood Red, Plate 1; under side—Carmine, Plate 1. Old foliage: upper side—Dark Cress Green, Plate 31; under side—Light Hellebore Green, Plate 17.
- *Shape.*—Oval pointed.
- *Texture.* — Upper side — leathery. Under side—smooth.

*Ribs and veins.*—Ordinary.
*Edge.*—Serrated (saw-toothed).
*Serration.*—Single; sharp.
*Leaf stem.*—Color—Courge Green, Plate 17. Under side—prickles.
*Stipules.*—Medium length; bearded.

Wood:
*New wood.* — Color — Liver Brown, Plate 14. Bark—smooth.
*Old wood.* — Color — Forest Green, Plate 17. Bark—smooth.

Thorns:
*Thorns.*—Quantity: on main stalks from base—ordinary; on laterals from stalk—ordinary.
Form—broad base; medium length; some straight and some hooked downward.

Color (when young)—Carmine, Plate 1.
Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by the vigorous habit of its plant growth, by its free-blooming habit, by the relatively large size of its blooms, and by the richness, intensity and distinctive color of its blooms.

No references cited.